(12) United States Patent
Gryska et al.

(10) Patent No.: US 10,267,758 B2
(45) Date of Patent: Apr. 23, 2019

(54) SENSOR ELEMENT, METHOD OF MAKING, AND METHOD OF USING THE SAME

(71) Applicant: 3M INNOVATIVE PROPERTIES COMPANY, St. Paul, MN (US)

(72) Inventors: Stefan H. Gryska, Woodbury, MN (US); Krzysztof A. Lewinski, Mahtomedi, MN (US); Michael C. Palazzotto, Woodbury, MN (US)

(73) Assignee: 3M INNOVATIVE PROPERTIES, COMPANY, St. Paul, MN (US)

( * ) Notice: Subject to any disclaimer, the term of this patent is extended or adjusted under 35 U.S.C. 154(b) by 54 days.

(21) Appl. No.: 14/406,727

(22) PCT Filed: Jun. 3, 2013

(86) PCT No.: PCT/US2013/043861
§ 371 (c)(1),
(2) Date: Dec. 9, 2014

(87) PCT Pub. No.: WO2014/003979
PCT Pub. Date: Jan. 3, 2014

(65) Prior Publication Data
US 2015/0168330 A1    Jun. 18, 2015

Related U.S. Application Data

(60) Provisional application No. 61/663,688, filed on Jun. 25, 2012.

(51) Int. Cl.
*G01N 25/18* (2006.01)
*G01N 27/22* (2006.01)
(Continued)

(52) U.S. Cl.
CPC .......... *G01N 27/228* (2013.01); *G01N 27/04* (2013.01); *G01N 27/223* (2013.01);
(Continued)

(58) Field of Classification Search
CPC .... G01N 27/228; G01N 27/04; G01N 27/223; G01N 27/226; G01N 33/0047; G01N 33/0062
(Continued)

(56) References Cited

U.S. PATENT DOCUMENTS 4,489,603 A * 12/1984 Fukami ............... G01N 27/121
                                                        200/61.06
4,662,220 A    5/1987 Laue
(Continued)

FOREIGN PATENT DOCUMENTS

JP    S51-80280 A    7/1976
JP    S58-044338 A   3/1983
(Continued)

OTHER PUBLICATIONS

Budd, P.M. (2004). "Polymers of intrinsic microporosity (PIMs)." Chem Comm. 230-231.*
(Continued)

*Primary Examiner* — Dennis White
(74) *Attorney, Agent, or Firm* — Yufeng Dong; Bradford B. Wright

(57) ABSTRACT

A sensor element includes first and second conductive electrodes that include interconnected carbon fibers. At least one or the first or second conductive electrodes is porous. The electrodes are separated by a porous dielectric detection layer including a sorbent material. Methods of making a sensor element and analyzing an analyte vapor are also disclosed.

7 Claims, 2 Drawing Sheets

(51) Int. Cl.
*G01N 27/04* (2006.01)
*G01N 33/00* (2006.01)
(52) U.S. Cl.
CPC ....... *G01N 27/226* (2013.01); *G01N 33/0047* (2013.01); *G01N 33/0062* (2013.01)
(58) Field of Classification Search
USPC .......................................................... 436/139
See application file for complete search history.

(56) References Cited

U.S. PATENT DOCUMENTS

| | | | |
|---|---|---|---|
| 5,036,704 | A | 8/1991 | Pusatcioglu |
| 5,536,486 | A | 7/1996 | Nagata |
| 7,297,445 | B2 | 11/2007 | Nakamura |
| 7,348,088 | B2 | 3/2008 | Hamrock |
| 7,510,626 | B2 * | 3/2009 | Hamada ................. D21H 13/50 162/138 |
| 7,632,589 | B2 | 12/2009 | Kawashima |
| 8,142,883 | B2 | 3/2012 | Chida |
| 8,378,694 | B2 | 2/2013 | David |
| 8,564,740 | B2 | 10/2013 | Schultz |
| 8,835,180 | B2 | 9/2014 | Gryska |
| 2006/0222840 | A1 | 10/2006 | Frisk |
| 2006/0246273 | A1 | 11/2006 | McKeown |
| 2007/0140907 | A1 | 6/2007 | Rakow et al. |
| 2008/0038589 | A1* | 2/2008 | Nakamura .......... H01M 4/8605 429/530 |
| 2009/0169959 | A1 | 7/2009 | Pierpont |
| 2011/0031983 | A1* | 2/2011 | David .................. G01N 27/125 324/663 |
| 2011/0045601 | A1* | 2/2011 | Gryska ................ G01N 27/221 436/149 |

FOREIGN PATENT DOCUMENTS

| | | |
|---|---|---|
| JP | 60-200152 A2 | 10/1985 |
| JP | S63-290950 A | 11/1988 |
| JP | 2003-232765 A | 8/2003 |
| JP | 2009-521675 T | 6/2009 |
| JP | 2010-540966 A | 12/2010 |
| JP | H04-21852 U | 6/2012 |
| WO | WO 2005-012397 | 2/2005 |
| WO | WO 2009-045733 | 4/2009 |
| WO | WO 2009-046011 | 4/2009 |
| WO | WO 2010-075333 | 7/2010 |
| WO | WO 2010075333 * | 7/2010 |
| WO | WO 2011-159480 | 12/2011 |
| WO | WO 2012-044419 | 4/2012 |
| WO | WO 2012-050686 | 4/2012 |
| WO | WO 2012-141883 | 10/2012 |
| WO | WO 2012-141894 | 10/2012 |
| WO | WO 2012-141925 | 10/2012 |
| WO | WO 2012-141958 | 10/2012 |
| WO | WO 2012-170248 | 12/2012 |
| WO | WO 2013-090188 | 6/2013 |

OTHER PUBLICATIONS

Budd, "Free volume and intrinsic microporosity in polymers" Journal of Materials Chemistry, 2005, vol. 15, pp. 1977-1986.
Budd, "Polymers of intrinsic microporosity (PIMs): robust, solution-processable, organic nanoporous materials", Chemical Communications, 2004, vol. 2, pp. 230-231.
Budd, "Solution-Processed, Organophilic Membrane Derived from a Polymer of Intrinsic Microporosity", Advanced Materials, 2004, vol. 16, No. 5, pp. 456-459.
Carta, "Novel Spirobisindanes for Use as Precursors to Polymers of Intrinsic Microporosity", Organic Letters, 2008, vol. 10, No. 13, pp. 2641-2643.
Chen, "A Capacitive Humidity Sensor Based on Multi-Wall Carbon Nanotubes", Sensors, 2009, vol. 9, pp. 7431-7444.
Ghanem, "High-Performance Membranes from Polyimides with Intrinsic Microporosity", Advanced Materials, 2008, vol. 20, pp. 2766-2771.
Ghanem, "Polymers of Intrinsic Microporosity Derived from Bis (phenazyl) Monomers", Macromolecules, 2008, vol. 41, pp. 1640-1646.
McKeown, "Polymers of Intrinsic Microporosity (PIMs)", Chemistry A European Journal, 2005, vol. 11, pp. 2610-2620.
Zampetti, "Design and optimization of an ultra thin flexible capacitive humidity sensor", Sensors and Actuators B, 2009, vol. 143, pp. 302-307.
International Search Report for PCT International Application No. PCT/US2013/043861, dated Sep. 23, 2013, 3pgs.

* cited by examiner

SENSOR ELEMENT, METHOD OF MAKING, AND METHOD OF USING THE SAME

FIELD

The present disclosure relates broadly to capacitive sensor elements suitable for analyzing an analyte vapor.

BACKGROUND

The detection of volatile organic compounds (VOCs) and humidity has many commercial, public, and residential applications due to environmental and safety concerns. One useful sensor type is a capacitive sensor in which a sorbent material is disposed between two electrodes. Typically, at least one of the electrodes is porous or otherwise permeable by the analyte vapor to be measured. Examples of sorbent materials used in these types of sensors include so-called Polymers of Intrinsic Microporosity (PIMs, for VOC measurement) and sulfonated fluoropolymers (for humidity measurement).

Conventionally, the electrodes are metal (e.g., gold) that are typically vapor-deposited, requiring a well-controlled vapor deposition process to produce electrodes with consistent porosity.

SUMMARY

In one aspect, the present disclosure provides a sensor element comprising:
  a first conductive electrode having inner and outer surfaces, wherein the first conductive electrode comprises interconnected carbon fibers;
  a second conductive electrode having inner and outer surfaces, wherein the second conductive electrode is porous and comprises interconnected carbon fibers, and wherein at least one of the first or second conductive electrodes is porous; and
  a porous dielectric detection layer having a thickness and disposed between the first and second conductive electrodes, wherein the porous dielectric detection layer comprises a sorbent material comprising an intrinsically microporous polymer containing dibenzodioxane linkages between monomeric units that are rigid, contorted, or rigid and contorted, and wherein the inner surfaces of the first and second conductive electrodes are separated by at least the thickness of the porous dielectric detection layer.

In another aspect, the present disclosure provides a method of making a sensor element, the method comprising:
  disposing a porous dielectric detection layer on a first conductive electrode, wherein the porous dielectric detection layer comprises a sorbent material, wherein the first conductive electrode has inner and outer surfaces, and wherein the first conductive electrode comprises interconnected carbon fibers;
  disposing a second conductive electrode on the porous dielectric detection layer, wherein the second conductive electrode has inner and outer surfaces, wherein the second conductive electrode comprises interconnected carbon fibers, and wherein at least one of the first or second conductive electrodes is porous; and
  wherein the porous dielectric detection layer has a thickness and is disposed between and contacts the first and second conductive electrodes, wherein the sorbent material comprises an intrinsically microporous polymer containing dibenzodioxane linkages between monomeric units that are rigid, contorted, or rigid and contorted, and wherein the inner surfaces of the first and second conductive electrodes are separated by at least the thickness of the porous dielectric detection layer.

Sensor elements according to the present disclosure are useful, for example, if connected to an operating circuit and incorporated into an electronic sensor.

Accordingly, in yet another embodiment, the present disclosure provides a method of analyzing an analyte vapor, the method comprising:
  providing a sensor element comprising:
    a first conductive electrode having inner and outer surfaces, wherein the first conductive electrode comprises interconnected carbon fibers;
    a second conductive electrode having inner and outer surfaces, wherein the second conductive electrode comprises interconnected carbon fibers, and wherein at least one of the first or second conductive electrodes is porous; and
    a porous dielectric detection layer having a thickness and disposed between the first and second conductive electrodes, wherein the porous dielectric detection layer comprises a sorbent material comprising an intrinsically microporous polymer containing dibenzodioxane linkages between monomeric units that are rigid, contorted, or rigid and contorted, and wherein the inner surfaces of the first and second conductive electrodes are separated by at least the thickness of the porous dielectric detection layer;
  exposing the sensor element to a gaseous sample comprising the analyte vapor;
  measuring at least one of capacitance or another electrical property of the sensor element; and
  based on said at least one of capacitance or another electrical property of the sensor element, determining at least one of the amount of the analyte vapor in the gaseous sample or the chemical identity of the analyte vapor.

Advantageously, the present disclosure eliminates altogether the need for metal electrodes in sensors (also known as capacitance sensors) by replacing them with carbon fiber paper and/or cloth. Carbon fiber paper and cloth are widely available from many manufacturers in different shapes and sizes, from rigid and brittle to thin and flexible (e.g., a nonwoven material). These materials feature different porosity and levels of gas permeability, and are used for applications ranging from fuel cells to air and water purification.

Additionally, sensor elements according to the present disclosure can be fabricated without mounting one of the conductive electrodes on a substrate that generally impedes or eliminates flow of the analyte vapor to the detection layer through that conductive electrode.

As used herein, the term "sorb" means to take up a liquid or a gas either by adsorption or by absorption.

As used herein, the term "carbon" refers to a bulk form of carbon (e.g., carbon black, lamp black, or graphite), unless it is referring to one or more carbon atoms in a chemical compound or formula.

Features and advantages of the present disclosure will be further understood upon consideration of the detailed description as well as the appended claims.

It should be understood that numerous other modifications and embodiments can be devised by those skilled in the art, which fall within the scope and spirit of the principles of the disclosure. The figure may not be drawn to scale.

DETAILED DESCRIPTION

Figure 1:
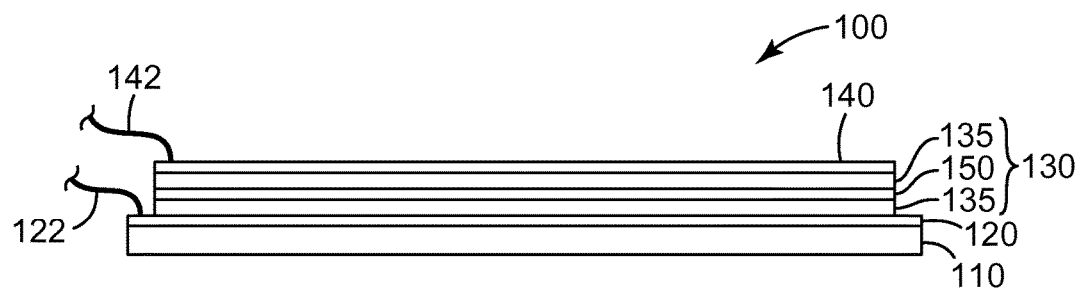
FIG. 1 is a schematic side view of an exemplary sensor element according to the present disclosure.

Referring now to FIG. 1, exemplary sensor element 100 comprises first conductive electrode 120 disposed on optional substrate 110, second conductive electrode 140, and detection layer 130, disposed between first conductive electrode 120 and second conductive electrode 140. At least one of first conductive electrode 120 or second conductive electrode 140 is porous, preferably both. Detection layer 130 comprises sorbent material 135 and optional porous dielectric separator 150 that prevents electrical shorts between first conductive electrode 120 and second conductive electrode 140. First conductive electrode 120 has inner and outer surfaces (122, 124) and is disposed on optional dielectric substrate 110. Second conductive electrode 140 has inner and outer surfaces (142, 144). First and second conductive members (122, 142) are electrically coupled to optional first and second conductive electrodes (120,140), respectively.

The first and second conductive electrodes are electrically conductive to a sufficient degree that they can serve as capacitor plates in the sensors element. Typically, the first and second conductive electrodes have a sheet resistance of less than about $10^7$ ohms/square (preferably less than $10^6$ or even less than $10^5$ ohms/square).

The first and/or second conductive electrodes are porous. In some embodiments, the first and/or second conductive electrodes may have a substantially uniform distribution of pores having an average pore size of less than 10 microns. In some embodiments, the first and/or second conductive electrodes have a larger and/or less uniform distribution of pore sizes. The inner surfaces of the first and second conductive electrodes have smooth inner surfaces. As used herein, the term "smooth" means that the surfaces lack structural irregularities of a size that is sufficient to cause an electrical short between the electrodes. Preferably, the first and second electrodes are dimensionally stable; that is, the electrodes cannot be stressed more than 10 percent (preferably cannot be stressed more than 5 percent, and more preferably cannot be stressed more than 2 percent) in any dimension without incurring permanent structural damage. The first and second conductive electrodes comprise interconnected carbon fibers. For example, the first and second conductive electrodes may comprise a carbon-fiber paper and/or other nonwoven material that comprises (or consists essentially of, or even consists of) carbon fibers. Carbon fiber paper is typically produced by allowing a liquid slurry of carbon fibers to drain through a continuously moving mesh. The resulting web is pressed and heated to produce paper veils or tissues from 20 g/m$^2$ to thick felts in excess of 250 g/m$^2$. These materials consist of a two-dimensional sheet of short fibers with a totally random arrangement within the plane of the sheet which is suitable for composite use, and are typically obtained in a form characterized by pores (e.g., micropores or nanopores) that permit passage of vapors through the material. Materials of this type have been used in gas diffusion membranes in fuel cell assemblies. Porous carbon fiber papers, useful in the first and second conductive of the present disclosure, are described in, for example, U.S. Pat. No. 7,297,445 (Nakamura et al.) and U.S. Pat. No. 7,510,626 (Hamada et al.), and U.S. Pat. No. 8,142,883 (Chida et al.). Likewise of porous carbon nonwovens (other than papers) can be found, for example, in U.S. Pat. No. 5,536,486 (Nagata et al.) and U.S. Pat. No. 7,632,589 (Kawashima et al.). Due to similarities in performance requirements, carbon fiber substrates that are useful in or as gas diffusion membranes such as those listed above are typically useful in practice of the present disclosure. Suitable carbon-fiber papers and nonwovens can be obtained from numerous commercial sources including for example, from: Toray Carbon Fibers America, Flower Mound, Tex.; Mitsubishi Rayon Co. Ltd. Tokyo, Japan; and Freudenberg and Co., Weinheim, Germany.

Hybrid carbon fiber papers including carbon/glass, carbon/aramid and carbon/cellulose, which consist of interpenetrating random fiber networks, have also been produced and may be used. In other embodiments, the first and second conductive electrodes may comprise a woven or knit cloth material formed of carbon fibers.

Preferably, the first and second conductive substrates are essentially free of carbon nanotubes. For example, they may comprise, on a total weight basis, less than 5 percent, less than 1 percent, or even less than 0.1 percent of carbon nanotubes. In some embodiments, the first and second electrodes are completely free of carbon nanotubes.

The first and second conductive electrodes may have any thickness. Preferably, the thickness of the first and/or second conductive electrodes is such that they can be handled, and in some cases may even allow sensor elements to be self-supporting (i.e., not needing a supporting substrate), although this is not a requirement. The first and second conductive electrodes may be the same or different.

In some embodiments, the inner surface of the first and/or conductive electrode(s) has a coating thereon that facilitates coating of the detection layer thereon, and/or lamination thereto. The coating may comprise an inorganic oxide and/or organic polymer, optionally further comprising particulate matter.

Examples of suitable inorganic oxides include silica, alumina, and titania, preferably in a microporous or mesoporous form.

In one exemplary embodiment, the coating comprises a fluoropolymer and optionally also carbon particles. Examples of suitable fluoropolymers include homopolymers and copolymers of vinylidene difluoride (VDF), tetrafluoroethylene (TFE), and hexafluoropropene (HFP) (e.g., terpolymers of VDF, TFE, and HFP), and copolymers of one or more of the foregoing monomers with ethylene, propylene, and/or a halogenated derivative thereof.

Examples of suitable carbon particles include particulate carbon blacks, thermal blacks, lamp blacks, channel blacks, and furnace blacks. Such materials are widely available from commercial sources.

One useful porous conductive carbon fiber paper, which has a smooth surface of a fluoropolymer coating with carbon particles dispersed therein coated on a carbon fiber paper is available as 3M 2979 MRC CP4, part no. 44-0050-2701-4 from 3M Company, St. Paul, Minn.

In some embodiments, the porous dielectric detection layer comprises a sorbent material comprising an intrinsically microporous polymer containing dibenzodioxane linkages between monomeric units that are rigid, contorted, or rigid and contorted. The porous dielectric detection layer spaces the first and second conductive electrodes apart so that they are not in electrical contact.

Optional porous dielectric separator 150, if present, serves to prevent electrical shorting between the first and second conductive electrodes. Preferably, it is sufficiently porous that an analyte can diffuse through its thickness; however, this is not a requirement. Preferably, the optional porous dielectric separator is at least coextensive with at least one of the first and second conductive electrodes, although this is not a requirement. Example of suitable materials for the separator include papers, microporous polymer films (e.g., microporous polypropylene films), and nonwovens (e.g., meltspuns or blown microfiber webs).

The optional dielectric substrate may comprise, for example, a continuous slab, layer, or film of dielectric material. It is disposed in sufficient proximity to the first conductive electrode that it may serve to provide physical strength and integrity to the sensor element. Any suitable dielectric material may be used, including, for example, glass, ceramic, and/or plastic. In large-scale production, a polymeric film such as, e.g., a polyester or polyimide film or sheet may be useful.

If desired, the first and/or second conductive electrodes may have a conductive lead (e.g., a wire) affixed thereto in electrical contact with the electrode. Preferably, the first and second conductive electrodes are at least substantially parallel (e.g., parallel), although this is not a requirement.

Sorbent material 135 can be any material (e.g., inorganic or organic) that is microporous and is capable of absorbing at least one analyte vapor within its interior. In this context, the terms "microporous" and "microporosity" mean that the material has a significant amount of internal, interconnected pore volume, with the mean pore size (as characterized, for example, by sorption isotherm procedures) being less than about 100 nm, typically less than about 10 nm. Such microporosity provides that molecules of the analyte (if present) will be able to penetrate the internal pore volume of the material and take up residence in the internal pores. The presence of such analyte in the internal pores can alter the dielectric properties of the material such that a change in the dielectric constant (or any other suitable electrical property) can be observed.

In some embodiments, the dielectric microporous material comprises a so-called Polymer of Intrinsic Microporosity (PIM). PIMs are polymeric materials with nanometer-scale pores due to inefficient packing of the polymer chains. For example, in Chemical Communications, 2004, (2), pp. 230-231, Budd et al. report a series of intrinsically microporous materials containing dibenzodioxane linkages between rigid and/or contorted monomeric building blocks (i.e., monomeric units). Representative members of this family of polymers include those generated by condensation of Component A (e.g., A1, A2, or A3) with Component B (e.g., B1, B2, or B3) as shown in Table 1 according to Scheme 1.

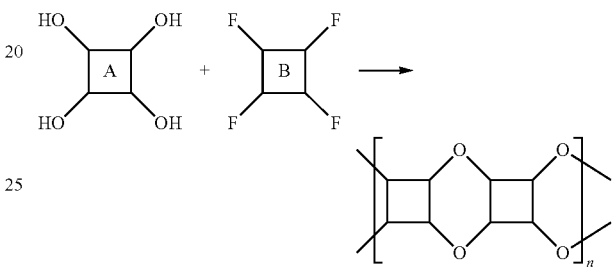

TABLE 1

COMPONENT A / COMPONENT B: A1/B1, A2/B2, A3/B3

Further suitable Components A and B, and resultant intrinsically microporous polymers, are known in the art, for example, as reported by Budd et al. in *Journal of Materials Chemistry*, 2005, Vol. 15, pp. 1977-1986; by McKeown et al. in *Chemistry, A European Journal*, 2005, Vol. 11, pp. 2610-2620; by Ghanem et al. in *Macromolecules*, 2008, vol.

41, pp. 1640-1646; by Ghanem et al. in *Advanced Materials*, 2008, vol. 20, pp. 2766-2771; by Carta et al. in *Organic Letters*, 2008, vol. 10(13), pp. 2641-2643; in PCT Published Application WO 2005/012397 A2 (McKeown et al.); and in U.S. Patent Appl. Publ. No. 2006/0246273 (McKeown et al.).

Such polymers can be synthesized, for example, by a step-growth polymerization where a bis-catechol such as, e.g., A1 (5,5',6,6'-tetrahydroxy-3,3,3',3'-tetramethyl-1,1'-spirobisindane) is allowed to react with a fluorinated arene such as, e.g., B1 (tetrafluoroterephthalonitrile) under basic conditions. Due to the rigidity and contorted nature of the backbone of the resulting polymers, these polymers are unable to pack tightly in the solid state and thus have at least 10 percent free volume and are intrinsically microporous.

PIMs may be blended with other materials. For example, a PIM may be blended with a material that itself is not an absorptive dielectric material. Even though not contributing to an analyte vapor response, such a material may be useful for other reasons. For example, such a material may allow the formation of a PIM-containing layer which has superior mechanical properties and the like. In one embodiment, PIMs may be dissolved in a common solvent with the other material to form a homogeneous solution, which may be cast to form an absorptive dielectric blend layer comprising both the PIM and the other polymer(s). PIMs may also be blended with a material that is an absorptive dielectric material (for example, zeolites, activated carbon, silica gel, hyper-cross-linked polymer networks and the like). Such materials may comprise insoluble materials that are suspended in a solution comprising of a PIMs material. Coating and drying of such a solution/suspension may provide a composite absorptive dielectric layer comprising both the PIM material and the additional absorptive dielectric material.

PIMs are typically soluble in organic solvents such as, for example, tetrahydrofuran, and can thus be cast as films from solution (e.g., by spin-coating, dip coating, or bar coating). However, characteristics (accessible thicknesses, optical clarity, and/or appearance) of films made from solutions of these polymers may vary markedly depending on the solvent or solvent system used to cast the film. For example, intrinsically microporous polymers of higher molecular weights may need to be cast from relatively unusual solvents (e.g., cyclohexene oxide, chlorobenzene, or tetrahydropyran) to generate films with desirable properties for use in vapor sensors as described herein. In addition to solution coating methods, the detection layer may be applied to the first conductive electrode by any other suitable method.

After a PIM is deposited (e.g., coated) or otherwise formed so as to comprise an absorptive dielectric layer, the material may be crosslinked using a suitable crosslinking agent such as, for example, bis(benzonitrile)palladium(II) dichloride. This process may render the absorptive dielectric layer insoluble in organic solvents, and/or may enhance certain physical properties such as durability, abrasion resistance, etc., which may be desirable in certain applications.

PIMs may be hydrophobic so that they will not absorb liquid water to an extent that the material swells significantly or otherwise exhibits a significant change in a physical property. Such hydrophobic properties are useful in providing an organic analyte vapor sensor element that is relatively insensitive to the presence of water. The material may however comprise relatively polar moieties for specific purposes.

Alternatively, in embodiments wherein the capacitive sensor element is used to detect humidity, the detection layer is preferably hydrophilic. For example, the detection layer may comprise a copolymer having monomeric units comprising

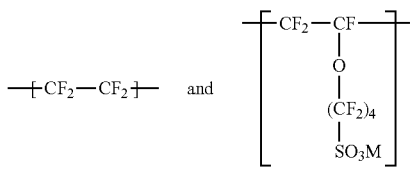

wherein M represents H (i.e., hydrogen), or an alkali metal (e.g., lithium, sodium, or potassium).

Such copolymers are described, for example, in U.S. Pat. No. 7,348,088 (Hamrock et al.). In one embodiment, the copolymer may be a random copolymer having a segment represented by the stoichiometric formula

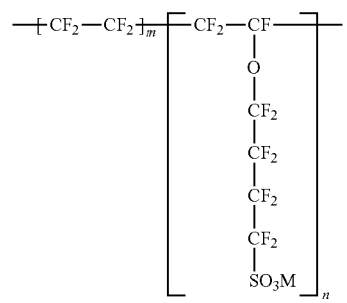

wherein m and n are positive integers (i.e., 1, 2, 3, etc.), and M is as previously defined. Other pendant groups such as, for example, perfluoroalkyl groups or perfluoroalkoxyl groups may also be present. Typically, substantially no (e.g., less than 5 mole percent of) other pendant groups are present in the copolymer; and more typically, no other pendant groups are present.

The copolymer may be made by the copolymerization of tetrafluoroethylene with 4'-fluorosulfonyl-1',1',2',2',3',3',4',4'-octafluorobutyloxy-1,2,2-trifluoroethylene (i.e., $CF_2=CFO(CF_2)_4SO_2F$) followed by basic hydrolysis of the sulfonyl fluoride to the alkali metal sulfonate form or the sulfonic acid form. Additional co-monomers may be included to provide perfluoroalkyl or perfluoroalkyl ether pendant groups in the copolymer. Vinylidene fluoride may also be used as a monomer. Polymerization can be accomplished by any suitable method, including aqueous emulsion polymerization. The copolymer typically may have a sulfonate equivalent weight (i.e., the weight of the copolymer having one —$SO_3M$ group) of at least 500 grams per sulfonate equivalent, more typically at least 650 grams per sulfonate equivalent, and more typically at least 750 grams per sulfonate equivalent. The copolymer typically has a sulfonate equivalent weight of less than 1200 grams per sulfonate equivalent, more typically less than 1100 grams per sulfonate equivalent, or even less than or equal to 1000 grams per sulfonate equivalent. In some embodiments, the copolymer has a sulfonate equivalent weight in a range of from 500 to 1000 grams per sulfonate equivalent.

Examples of commercially available copolymers include those available under the trade designation 3M PERFLUOROSULFONIC ACID IONOMER from 3M Company, Saint Paul, Minn.

The detection layer may be deposited (for example, on the conductive electrode) by any suitable technique. Casting out of solvent or water, followed by heating to dry and optionally anneal the detection layer is typically an effective method. If desired, a fluorosulfonylated copolymer precursor may be cast out of solvent followed by hydrolysis, as discussed above.

Further details concerning an absorptive capacitance sensor element wherein the dielectric microporous material is an organosilicate material is described in PCT Publication No. WO 2010/075333 A2 (Thomas).

The detection layer may have any thickness, but typically is in a range of from about 100 nanometers (nm) to 1 millimeter. More typically, the detection layer has a thickness in a range of from 500 nm to 10 microns, or even from 700 to 3500 nm.

Further details concerning fabrication of absorptive capacitance sensor elements including PIMs, and principles of their operation, can be found in, for example, U.S. Patent Appl. Publ. Nos. 2011/0045601 A1 (Gryska et al.) and 2011/0031983 A1 (David et al.), and U.S. Provisional Appln. No. 61/388,146 entitled "Sensor Element, Method of Making the Same, and Sensor Device Including the Same" (Palazzotto et al.).

The detection layer may contain one or more additional components such as, for example, colorants, residual organic solvent, fillers, and/or plasticizers.

In one embodiment, the dielectric microporous material comprises a continuous matrix. Such a matrix is defined as an assembly (e.g., a coating, layer, etc.) in which the solid portion of the material is continuously interconnected (irrespective of the presence of porosity as described above, or of the presence of optional additives as discussed below). That is, a continuous matrix is distinguishable from an assembly that comprises an aggregation of particles (e.g., zeolites, activated carbons, or carbon nanotubes). For example, a layer or coating deposited from a solution will typically comprise a continuous matrix (even if the coating itself is applied in a patterned manner and/or comprises particulate additives). A collection of particles deposited via powder spraying, coating and drying of a dispersion (e.g., a latex), or by coating and drying of a sol-gel mixture, may not comprise a continuous network. However, if such a latex, sol-gel, etc., layer can be consolidated such that individual particles are no longer discernible, nor is it possible to discern areas of the assembly that were obtained from different particles, such a layer may then be considered to be a continuous matrix.

Capacitance-related property sensor elements according to the present disclosure can be made, for example, by disposing the first conductive electrode on the optional dielectric substrate (e.g., by adhering with adhesive tape, glue). In some embodiments, the optional substrate may be used during fabrication of the sensor elements, and later removed. In such cases, it is preferably removably adhered to the first conductive electrode.

Next, dielectric microporous material in a suitable organic solvent is deposited onto the first conductive electrode, typically as a solution in a solvent using a solvent coating method, and any residual solvent is at least substantially removed. Alternatively, if detection layer is in film form, heat and/or pressure lamination may be used. Finally, the second conductive electrode is disposed on the dielectric microporous material, typically by heat and/or pressure lamination. Such general methods of coating and lamination are well known in the art. To facilitate connection to an operating circuit, it may be desirable to attach a conductive lead (e.g., a metal wire, pin, socket, or other terminal) to each of the first and second conductive electrodes.

The present disclosure also provides methods of analyzing an analyte vapor. The method comprises: providing a sensor element according to the present disclosure (i.e., with a detection layer capable of sorbing an organic compound vapor and/or water vapor); exposing the sensor element to the analyte vapor; and then measuring at least one of capacitance or another electrical property of the sensor element. In order to measure capacitance or another electrical property of the sensor element, the first and second conductive electrodes are electrically connected to an operating circuit capably of determining, and preferably displaying, the desired electrical property (e.g., capacitance).

If desired, the sensor element may be heated at a temperature above ambient (e.g., at least 30° C., at least 40° C., or even at least 50° C.) in order to remove variability due to changes in temperature. Generally, the sensor element should be calibrated using known concentrations of an analyte vapor to be measured (thereby generating calibration data) and a reference zero concentration (i.e., reference baseline) to ensure accuracy. In use, the sensor element is exposed to the analyte vapor and typically allowed sufficient time to equilibrate, although this is not a requirement. Then, the capacitance (or other electrical property) is measured and the reference baseline is subtracted to give a corrected capacitance which may be compared directly or indirectly with the appropriate calibration data to determine the vapor concentration and/or identity of the analyte vapor. If desired, a sample containing the analyte vapor may be split into multiple dilutions that are analyzed to generate a response curve for comparison with reference data.

Suitable operating circuits are well known in the art and include, for example, LCR meters, multimeters, and other electronic measurement devices. In this context, the term "operating circuit" refers generally to an electrical apparatus that can be used to apply a voltage to the first conductive electrode and the second conductive electrode (thus imparting a charge differential to the electrodes), and/or to monitor an electrical property of the sensor element, wherein the electrical property may change in response to the presence of an organic analyte. In various embodiments, the operating circuit may monitor any or a combination of inductance, capacitance, voltage, resistance, conductance, current, impedance, phase angle, loss factor, or dissipation.

Such an operating circuit may comprise a single apparatus which both applies voltage to the electrodes, and monitors an electrical property. In an alternative embodiment, such an operating circuit may comprise two separate apparatuses, one to provide voltage, and one to monitor the signal. The operating circuit is typically electrically coupled to first conductive electrode and to second conductive electrode by conductive members.

Further details concerning measurement of analyte vapors using capacitive sensor elements can be found in, for example, U.S. Provisional Appl. Nos. 61/475,014 entitled "Electronic Device Including Calibration Information and Method of Using the Same" (Kang et al.); 61/475,000 entitled "Method of Detecting Volatile Organic Compounds" (Kang et al.); 61/475,009 entitled "Vapor Sensor Including Sensor Element with Integral Heating" (Palazzotto et al.); 61/494,578 entitled "Humidity Sensor and Sensor Element Therefor" (Gryska et al.); and 61/569,987 entitled "Method for Identification and Quantitative Determination of an Unknown Organic Compound in a Gaseous Medium" (Gryska et al.).

Select Embodiments of the Present Disclosure

In a first embodiment, the present disclosure provides a sensor element comprising:
a first conductive electrode having inner and outer surfaces, wherein the first conductive electrode comprises interconnected carbon fibers;
a second conductive electrode having inner and outer surfaces, wherein the second conductive electrode is porous and comprises interconnected carbon fibers, and wherein at least one of the first or second conductive electrodes is porous; and
a porous dielectric detection layer having a thickness and disposed between the first and second conductive electrodes, wherein the porous dielectric detection layer comprises a sorbent material comprising an intrinsically microporous polymer containing dibenzodioxane linkages between monomeric units that are rigid, contorted, or rigid and contorted, and wherein the inner surfaces of the first and second conductive electrodes are separated by at least the thickness of the porous dielectric detection layer.

In a second embodiment, the present disclosure provides a sensor element according to the first embodiment, wherein the inner surface of at least one of the first or second conductive electrode is smooth.

In a third embodiment, the present disclosure provides a sensor element according to the first or second embodiment, wherein a porous dielectric separator is disposed in the sorbent material.

In a fourth embodiment, the present disclosure provides a sensor element according to any one of the first to third embodiments, wherein at least one of the first and second conductive electrodes comprises a nonwoven carbon fabric or carbon paper.

In a fifth embodiment, the present disclosure provides a sensor element according to the fourth embodiment, wherein said nonwoven carbon fabric or carbon paper has a coating thereon comprising a fluoropolymer.

In a sixth embodiment, the present disclosure provides a sensor element according to the fifth embodiment, wherein the coating further comprises carbon particles.

In a seventh embodiment, the present disclosure provides a sensor element according to any one of the first to sixth embodiments, further comprising a first conductive lead in electrical communication with the first conductive electrode, and a second conductive lead in electrical communication with the second conductive electrode.

In an eighth embodiment, the present disclosure provides a method of making a sensor element, the method comprising:
disposing a porous dielectric detection layer on a first conductive electrode, wherein the porous dielectric detection layer comprises a sorbent material, wherein the first conductive electrode has inner and outer surfaces, and wherein the first conductive electrode comprises interconnected carbon fibers;
disposing a second conductive electrode on the porous dielectric detection layer, wherein the second conductive electrode has inner and outer surfaces, wherein the second conductive electrode comprises interconnected carbon fibers, and wherein at least one of the first or second conductive electrodes is porous; and
wherein the porous dielectric detection layer has a thickness and is disposed between and contacts the first and second conductive electrodes, wherein the sorbent material comprises an intrinsically microporous polymer containing dibenzodioxane linkages between monomeric units that are rigid, contorted, or rigid and contorted, and wherein the inner surfaces of the first and second conductive electrodes are separated by at least the thickness of the porous dielectric detection layer.

In a ninth embodiment, the present disclosure provides a method according to the eighth embodiment, wherein the inner surface of at least one of the first or second conductive electrode is smooth.

In a tenth embodiment, the present disclosure provides a method according to the eighth or ninth embodiment, wherein a porous dielectric separator is disposed in the sorbent material.

In an eleventh embodiment, the present disclosure provides a method according to any one of the eighth to tenth embodiments, wherein at least one of the first and second conductive electrodes comprises a nonwoven carbon fabric or carbon paper.

In a twelfth embodiment, the present disclosure provides a method according to the eleventh embodiment, wherein said nonwoven carbon fabric or carbon paper has a coating thereon comprising a fluoropolymer.

In a thirteenth embodiment, the present disclosure provides a method according to the twelfth embodiment, wherein the coating further comprises carbon particles.

In a fourteenth embodiment, the present disclosure provides a method according to any one of the eighth to thirteenth embodiments, further comprising:
attaching a first conductive lead to the first conductive electrode, and a second conductive lead to the second conductive electrode.

In a fifteenth embodiment, the present disclosure provides a method of analyzing an analyte vapor, the method comprising:
providing a sensor element comprising:
a first conductive electrode having inner and outer surfaces, wherein the first conductive electrode comprises interconnected carbon fibers;
a second conductive electrode having inner and outer surfaces, wherein the second conductive electrode comprises interconnected carbon fibers, and wherein at least one of the first or second conductive electrodes is porous; and
a porous dielectric detection layer having a thickness and disposed between the first and second conductive electrodes, wherein the porous dielectric detection layer comprises a sorbent material comprising an intrinsically microporous polymer containing dibenzodioxane linkages between monomeric units that are rigid, contorted, or rigid and contorted, and wherein the inner surfaces of the first and second conductive electrodes are separated by at least the thickness of the porous dielectric detection layer;
exposing the sensor element to a gaseous sample comprising the analyte vapor;
measuring at least one of capacitance or another electrical property of the sensor element; and
based on said at least one of capacitance or another electrical property of the sensor element, determining at least one of the amount of the analyte vapor in the gaseous sample or the chemical identity of the analyte vapor.

In a sixteenth embodiment, the present disclosure provides a method according to the fifteenth embodiment, wherein the inner surface of at least one of the first or second conductive electrode is smooth.

In a seventeenth embodiment, the present disclosure provides a method according to the fifteenth or sixteenth embodiment, wherein a porous dielectric separator is disposed in the sorbent material.

In an eighteenth embodiment, the present disclosure provides a method according to any one of the fifteenth to seventeenth embodiments, wherein at least one of the first and second conductive electrodes comprises a nonwoven carbon fabric or carbon paper.

In a nineteenth embodiment, the present disclosure provides a method according to the eighteenth embodiment, wherein said nonwoven carbon fabric or carbon paper has a coating thereon comprising a fluoropolymer.

In a twentieth embodiment, the present disclosure provides a method according to the nineteenth embodiment, wherein the coating further comprises carbon particles.

In a twenty-first embodiment, the present disclosure provides a method according to any one of the fifteenth to twentieth embodiments, wherein the sensor element further comprises a first conductive lead in electrical communication with the first conductive electrode, and a second conductive lead in electrical communication with the second conductive electrode.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.
Test Methods
VOC Measurement Test Method A simple flow-through delivery system was used to deliver known concentrations of methyl ethyl ketone (MEK) to the sensor for measurement. Polytetrafluoroethylene (ptfe) tubing was used throughout the delivery system. The exposure concentrations were generated by metering MEK flow into the evaporation flask by means of a syringe pump and 5 ml gastight syringe. The evaporation flask contained 42.5 mm diameter #1 type filter paper to enhance the evaporation process in conjunction with 10 L/min stream of dry air controlled by a gas flow meter. The calculations for the set points of a syringe pump and the flow rate for the air (to get the desired concentration of MEK vapors) were done according to the methods in "Gas Mixtures: Preparation and Control" (Gary O. Nelson: Lewis Publishers, Boca Raton, Fla., 1992). The concentration of MEK in the gaseous stream was monitored with an infrared spectrometer (Miran Sapphire infrared spectrometer from ThermoElectron of Waltham, Mass.). The gaseous MEK stream was introduced into a test chamber (held at controlled temperature) containing the sensor. The electrodes of the sensor were connected to an operating circuit that comprised an LCR meter (available as Instek Model 821 LCR meter from Instek America, Corp. Chino, Calif.) using spring-loaded probes. The changes in capacitance (in picofarads (pF)) of the sensor were monitored at a frequency of 1 kHz and 1 V at specific time intervals during the entire course of the VOC vapor test.
% Relative Humidity (% R.H.) Measurement Test Method A simple flow-through delivery system was used to deliver known levels of % R.H. to the sensor for measurement. Ptfe tubing was used throughout the delivery system. The exposure concentrations were generated by 10 L/min flow of air through temperature controlled evaporation flask containing distilled water. The temperature of the water in the double wall flask was controlled by a Heating/Cooling Circulator from VWR, and the air stream of dry air was regulated by a Matheson gas flow meter. The % R.H. level in the gaseous stream was monitored with an iTHX-M Humidity Meter available from Omega Engineering Inc., Stamford, Conn. The humidified air was introduced into a test chamber (held at controlled temperature) containing the sensor. The electrodes of the sensor were connected to an operating circuit that comprised an LCR meter (available under the designation Instek Model 821 LCR meter from Instek America, Corp. Chino, Calif.) using spring-loaded probes. The changes in capacitance (in picofarads (pF)) of the sensor were monitored at a frequency of 1 kHz and 1 V at specific time intervals during the entire course of the water vapor test. The choice of such low operating potential and high perturbation frequency ensured lack of interference from any possible Faradaic processes associated with electrolyzing water present in the measured gas stream.
Preparation of PIM Material PIM material was prepared from the monomers 5,5',6,6'-tetrahydroxy-3,3,3',3'-tetramethyl-1,1'-spirobisindane and tetrafluoroterephthalonitrile generally according to the procedure reported by Budd et al. in *Advanced Materials,* 2004, Vol. 16, No. 5, pp. 456-459. 40.000 grams of 5,5',6,6'-tetrahydroxy-3,3,3',3'-tetramethyl-1,1'-spirobisindane were combined with 23.724 g of tetrafluoroterephthalonitrile, 97.373 g potassium carbonate, and 1016.8 g of N,N-dimethylformamide, and the mixture was reacted at 68° C. for 72 hours. The polymerization mixture was poured into water, and the precipitate was isolated by vacuum filtration. The resulting polymer was twice dissolved in tetrahydrofuran, precipitated from methanol, and air dried at room temperature. A yellow solid product was obtained having a number-average molecular weight of approximately 41,900 g/mol, as determined by gel permeation chromatography analysis using light scattering detection.

Example 1

This example describes the preparation of a PIM-based sensor element. A solution of 5.5 percent by weight PIM (prepared as described above) in chlorobenzene was prepared by mixing the components in a small jar and placing it on a roller mill (Mini Bottle Roller number 348920 from Wheaton Science Products, Millville, N.J.) for about 3 hours then filtering through an ACRODISC 25 MM SYRINGE FILTER WITH 1 MICRON GLASS FIBER MEMBRANE filter disk from PALL Life Sciences, Ann Arbor, Mich. The solution was allowed to sit over night so that any bubbles that formed could escape. The PIM solution was then used in the preparation of all samples.

Figure 2:
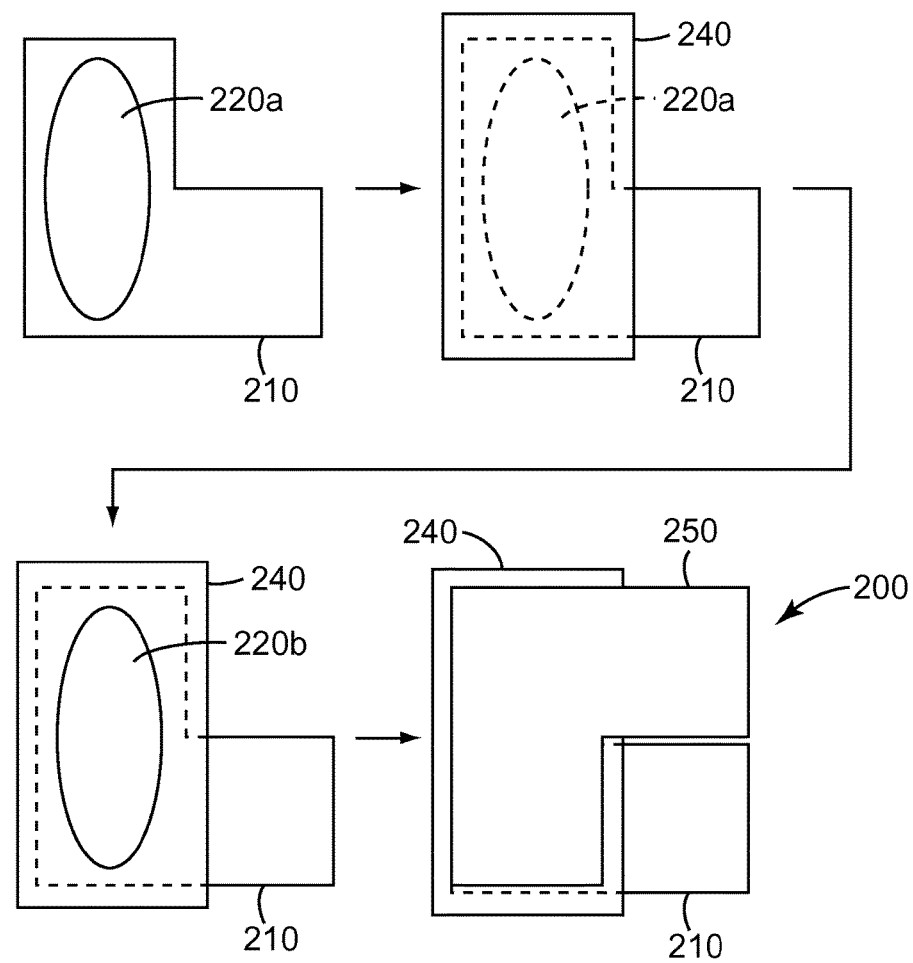
FIG. 2 is a schematic process flow diagram showing the process used in Example 1.

Sensor elements were prepared as shown in FIG. 2, using conductive, porous carbon paper (3M 2979 MRC CP4, part no. 44-0050-2701-4) obtained from 3M Company, St. Paul, Minn. From a disposable transfer pipette 3 droplets of PIM solution 220a were deposited on the smoothest surface of the L-shaped piece of the carbon paper (bottom electrode 210) that was 0.21 mm thick, 25 mm long, and 12 mm wide. Next, a rectangular piece (27 mm×14 mm) of 0.1 mm thick HammerMill printer paper (part no. 00500-7) 230 available from International Paper, Memphis, Tenn., was placed over the PIM solution. This step caused the solvent to wet the paper and evenly spread over the bottom electrode. Next, an additional 3 droplets of the PIM solution 220b were deposited directly on paper 240 and allowed to spread. In the final step the top electrode 250, composed of the same material as bottom electrode 210, was set on top of the PIM material with the smoothest side down, and gentle pressure was applied. After 1 hour of drying at room temperature, the assembly was heated for additional 1 hour in a 100° C. oven resulting in sensor element 200. The total thickness of the sensor was 0.55 mm. The paper spacer was only included to prevent possible electrical shorts between the top and the bottom electrodes.

Example 2

This example demonstrates the preparation of an ionomer-based sensor element. A 20% solids by weight in 60/40 by weight n-propanol/water solution of 825 g/equiv (equivalent weight) 3M PERFLUOROSULFONIC ACID IONOMER was prepared by mixing the components in a small jar and placing it on a roller mill (MINI BOTTLE ROLLER, part no. 348920, from Wheaton Science Products, Millville, N.J.) for about 4 hours, then filtering through an ACRODISC 25 MM SYRINGE FILTER WITH 1 MICRON GLASS FIBER MEMBRANE filter disk from Pall Life Sciences, Ann Arbor, Mich. The solution was allowed to sit over night so that any bubbles that formed could escape. The solution (330) was then used in the preparation of all samples.

Figure 3:
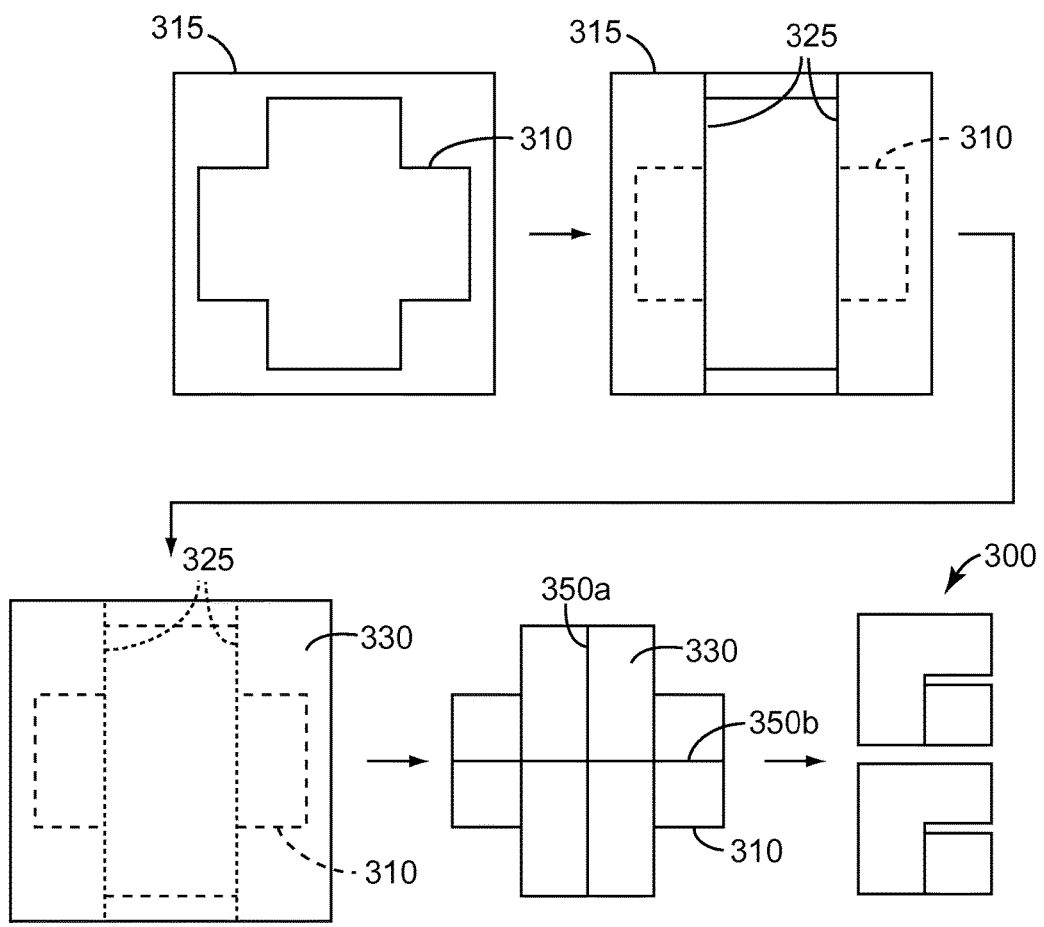
FIG. 3 is a schematic process flow diagram showing the process used in Example 2.

Assembly of sensor element 300 is shown in FIG. 3. Sensor elements were prepared using porous conductive carbon fiber paper (3M 2979 MRC CP4, part no. 44-0050-2701-4) obtained from 3M Company, St. Paul, Minn. From this 0.21 mm thick carbon paper a symmetrical cross (310) of size 50 mm×50 mm was cut out and placed on 60 mm×60 mm piece of cardboard (315). Next, to protect part of the material from the coating solution, two sides of the cross were covered and taped down to the cardboard using 0.75 inch wide Magic Tape #105 transparent tape (325) from 3M Company. At this point, the smoothest surface of the porous conductive carbon fiber paper was facing up. Samples were then spin-coated with ionomer solution (330) using a Model WS 400B-8NPP/LITE spin coater from Laurell Technologies Corporation of North Wales, Pa. To coat a sample, it was placed in the spin coater and about 1 ml of ionomer solution was put on the sample. Each sample was spun for 60 seconds at 1000 rpm. Then, another 1 ml of the ionomer solution was put on and spun for 60 seconds at 4000 rpm. In the next step, the tape was peeled off, and the coated carbon paper was removed from the cardboard and divided with scissors into four pieces along cuts 350a and 350b. Two diagonal sections were then "sandwiched" together to construct two sensor elements 300 that were then cured for 15 minutes in 150° C. oven. The total thickness of each sensor element was 0.50 mm.

Example 3

A sensor element according to Example 1 was prepared and tested according to the VOC Measurement Test Method. Before testing, sensor was heated for 15 minutes at 150° C. in an oven. Capacitance measurements were made with MEK vapor in dry air at 50, 100, 200, 400 and 800 parts per million (ppm) with 20 minutes exposure time for each concentration. MEK exposure showed good sensor sensitivity over a wide range of concentration.

These experimental results are reported in the form of $\Delta C/C_O$ versus concentration in Table 1 (below), wherein $C_O$ is the sensor element baseline capacitance at the same temperature in the absence of MEK, and $\Delta C$ is the difference between the measured capacitance and the baseline capacitance.

TABLE 1

| MEK Concentration, ppm | Example 3, $\Delta C/C_o$ |
|---|---|
| 50 | 0.023 |
| 100 | 0.062 |
| 200 | 0.110 |
| 400 | 0.156 |
| 800 | 0.187 |

Example 4

A sensor element according to Example 2 was prepared and tested according to the % Relative Humidity Measurement Test Method. Before making measurements, the sensor element was heated for 15 minutes in 150° C. oven. Measurements were made with different levels of relative humidity ranging from 0.0% to 85.1%, and then back down to 0.0%. Moisture exposure showed good sensitivity of the sensor element over a wide range of % RH that was comparable to an iTHX-M Humidity Meter from Omega Engineering, Inc. Results are reported in Table 2 (below), wherein $C_O$ is the sensor element baseline capacitance at the same temperature in the absence of water vapor, and $\Delta C$ is the difference between the measured capacitance and the baseline capacitance.

TABLE 2

| iTHX-M Humidity Meter, % R.H. | Example 4, $\Delta C/C_o$ |
|---|---|
| 0.0 | 0.2 |
| 5.1 | 89.8 |
| 7.0 | 400.0 |
| 15.1 | 2140.4 |
| 20.4 | 3806.3 |
| 28.4 | 6825.1 |
| 41.4 | 11492.2 |
| 53.7 | 14717.7 |
| 65.4 | 17143.0 |
| 80.1 | 19043.5 |
| 85.1 | 19402.4 |
| 74.4 | 18178.2 |
| 58.2 | 16189.3 |
| 45.0 | 13920.7 |
| 35.0 | 11473.8 |
| 25.0 | 8305.4 |
| 15.0 | 4302.9 |
| 11.5 | 3876.0 |
| 10.0 | 3675.4 |
| 7.0 | 1385.8 |
| 3.6 | 890.2 |
| 0.0 | 1.9 |

Other modifications and variations to the present disclosure may be practiced by those of ordinary skill in the art, without departing from the spirit and scope of the present disclosure, which is more particularly set forth in the appended claims. It is understood that aspects of the various embodiments may be interchanged in whole or part or combined with other aspects of the various embodiments. All cited references, patents, or patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. A sensor element having no metal electrodes, the sensor element comprising:
   a first conductive electrode having inner and outer surfaces, wherein the first conductive electrode comprises interconnected carbon fibers;
   a second conductive electrode having inner and outer surfaces, wherein the second conductive electrode comprises interconnected carbon fibers, and wherein at least one of the first or second conductive electrodes is porous; and
   a porous dielectric detection layer having a thickness and disposed between the first and second conductive electrodes, wherein the porous dielectric detection layer comprises a sorbent material comprising a polymer of intrinsic microporosity (PIM) containing dibenzodioxane linkages between monomeric units that are rigid, contorted, or rigid and contorted, and wherein the inner surfaces of the first and second conductive electrodes are separated by at least the thickness of the porous dielectric detection layer,
   wherein a porous dielectric separator layer is disposed in the PIM of the porous dielectric detection layer to prevent electrical shorting between the first and second conductive electrodes, the porous dielectric separator layer comprises a layer of paper, a microporous polymer film, or a layer of nonwoven material, the PIM is disposed at least on both sides of the porous dielectric separator layer, and
   wherein the first conductive electrode, the porous dielectric detection layer including the porous dielectric separator layer, and the second conductive electrode are arranged in this order as a flexible layered structure to work as a capacitance sensor, and the first and second conductive electrodes are not metal electrodes.

2. The sensor element of claim 1, wherein the inner surface of at least one of the first or second conductive electrode is smooth.

3. The sensor element of claim 1, wherein at least one of the first and second conductive electrodes comprises a nonwoven carbon fabric or carbon paper.

4. The sensor element of claim 3, wherein said nonwoven carbon fabric or carbon paper has a coating thereon comprising a fluoropolymer.

5. The sensor element of claim 4, wherein the coating further comprises carbon particles.

6. The sensor element of claim 1, further comprising a first conductive lead in electrical communication with the first conductive electrode, and a second conductive lead in electrical communication with the second conductive electrode.

7. The sensor element of claim 1, wherein the first and second conductive electrodes each consists essentially of carbon fibers.

* * * * *

UNITED STATES PATENT AND TRADEMARK OFFICE
CERTIFICATE OF CORRECTION

PATENT NO. : 10,267,758 B2  
APPLICATION NO. : 14/406727  
DATED : April 23, 2019  
INVENTOR(S) : Stefan Gryska Page 1 of 1

It is certified that error appears in the above-identified patent and that said Letters Patent is hereby corrected as shown below:

On the Title Page

Column 1  
Item (73), Assignee, delete "Properties," and insert -- Properties --, therefore.

Signed and Sealed this  
Twelfth Day of May, 2020

Andrei Iancu  
*Director of the United States Patent and Trademark Office*